(12) United States Patent
McCormick

(10) Patent No.: US 7,144,713 B1
(45) Date of Patent: Dec. 5, 2006

(54) METHOD FOR PRECIPITATING NUCLEIC ACID WITH VISIBLE CARRIER

(75) Inventor: Mark R. McCormick, Madison, WI (US)

(73) Assignee: EMD Biosciences, Inc., Madison, WI (US)

( * ) Notice: Subject to any disclaimer, the term of this patent is extended or adjusted under 35 U.S.C. 154(b) by 15 days.

(21) Appl. No.: 08/724,631

(22) Filed: Oct. 1, 1996

Related U.S. Application Data

(60) Provisional application No. 60/004,668, filed on Oct. 2, 1995.

(51) Int. Cl.
*C12P 19/34* (2006.01)

(52) U.S. Cl. .................. 435/91.1; 536/25.41; 536/102; 536/124; 536/127

(58) Field of Classification Search ................ 536/124, 536/127, 102, 25.41; 514/60; 435/91.1
See application file for complete search history.

(56) References Cited

U.S. PATENT DOCUMENTS

| | | | | |
|---|---|---|---|---|
| 4,435,429 A | * | 3/1984 | Burrows et al. | 426/18 |
| 4,769,327 A | * | 9/1988 | Stephens et al. | 435/68 |
| 4,927,644 A | * | 5/1990 | Arbige et al. | 426/35 |
| 5,288,845 A | | 2/1994 | Chakraborty et al. | |

FOREIGN PATENT DOCUMENTS

WO    WO97/07207    2/1997

OTHER PUBLICATIONS

Hengen, Paul N. Trends in Biochemical Sciences 21:224-225, Jun. 1996.*

Gaillard et al. Nucl. Acids Res. vol. 18, No. 2, p. 378, 1990.*
Sotiroudis, T. et al "Phosphorylase b covalently bound to glycogen . . . " Eur. J. Biochem. (1978) vol. 88, pp. 573-581.*
Abdel-Akher, et al., "The Repeating Unit of Glycogen," *Journal of the American Chemical Society*, 73:994-996 (1950).
Aldrich, "Catalog Handbook of Fine Chemicals," pp. 642, 949, 1008 and 1135 (1990-1991).
Bahl, et al., "Studies on the Anomalous Linkages in Glycogen and Amylopectin," *Organic Chemistry*, 31:2915-2920 (1966).
Bell, et al., "Observations on the Chemistry of Liver Glycogen," *Biochem. Journal*, 28:882-889 (1934).
Gallagher, et al., "Carrier RNA Enhancement of Recovery of DNA from Dilute Solutions," *Biochemical and Biophysical Research Communications*, 144-1:271-276 (1987).
Hamilton, et al., "Reduction of the Products of Periodate Oxidation of Carbohydrates. III. The Constitution of Amylopectin," *Journal of American Chemical Society*, 78:5910-5912 (1956).
Wallace, "Percipitation of Nucleic Acids," *Method in Enzymology*, 152:41-48 (1987).
"Product Summary for Quik-Precip," Advanced Genetic Technologies Corp.
"Amine-Containing Reactive Probes, Including the Hydrazines," *Molecular Probes Catalog '92-'94*, pp. 42-49.
"pH Indicators," *Molecular Probes Catalog '92-'94*, pp. 129-141.
"Dextrans," *Molecular Probes Catalog '92-'94*, pp. 185-192.
"Alphabetical List of Compounds," *Sigma Chemical Company Catalog*, p. 506.

* cited by examiner

*Primary Examiner*—Leigh C. Maier
(74) *Attorney, Agent, or Firm*—Foley & Lardner LLP

(57) ABSTRACT

A suitable carrier molecule useful in a nucleic acid precipitation method is modified by coupling a suitable visualizable indicator molecule to the carrier molecule. The conjugated carrier facilitates nucleic acid precipitation because the presence and location of nucleic acid in a sample is readily observed and monitored.

12 Claims, 1 Drawing Sheet

METHOD FOR PRECIPITATING NUCLEIC ACID WITH VISIBLE CARRIER

CROSS-REFERENCE TO RELATED APPLICATIONS

This application claims the benefit of prior provisional patent application No. 60/004,668, filed Oct. 2, 1995.

STATEMENT REGARDING FEDERALLY SPONSORED RESEARCH OR DEVELOPMENT

Not applicable.

BACKGROUND OF THE INVENTION

Precipitation of nucleic acids is a common procedure in molecular biology research. Precipitation is often necessary to concentrate dilute solutions of a nucleic acid or to change the solvent in which the nucleic acid is dissolved. In practice, a salt is added to the nucleic acid solution followed by a suitable amount of an alcohol such as ethanol or isopropanol. The sample is incubated at a suitable temperature until nucleic acid molecules precipitate. The nucleic acid is then harvested by centrifugation.

When working with dilute nucleic acid solutions ($\leqq 10$ μg/ml) or small amounts of DNA or RNA ($\leqq 1$ μg), it is often desirable to increase the precipitation efficiency by including a carrier molecule. In addition, carriers can increase the precipitation rate and can reduce the overall time necessary to recover a nucleic acid from solution. A carrier molecule can increase the amount of material recovered from dilute solutions or increase recovery of small amounts of nucleic acids.

Wallace, D. M., (1987) Meth. Enzymol. 152, 41–48 reviewed the requirements and strategies used to precipitate nucleic acids. Wallace is incorporated herein by reference as background to the present invention. Wallace reports the use of carrier molecules such as transfer RNA (tRNA) and purified glycogen to increase the nucleic acid precipitation rate and efficiency.

Glycogen is a high molecular weight polysaccharide composed of repeating units of D-glucopyranose residues joined by $(1 \rightarrow 4)$-α-D-glucosidic linkages with branch points at position C-6 at one out of 12 residues on average. The branch lengths are in the range of 4–8 residues (Bahl, O. P. and Smith, F. J., (1966) Org. Chem., 31, 2915–2920). The base structure (excluding branch structures) is:

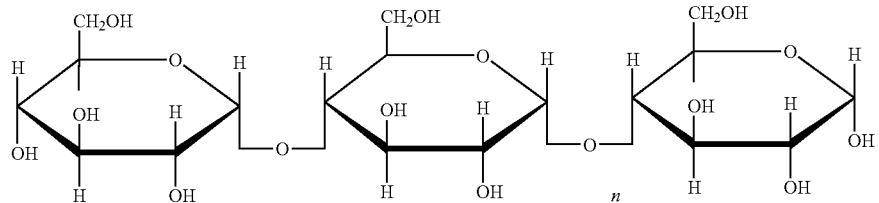

Glycogen is recognized to be a good carrier in nucleic acid precipitation methods because it shares solubility and precipitation characteristics with nucleic acids. Since a nucleic acid backbone is also composed of repeating units, namely ribose or deoxyribose connected via phosphodiester linkages, both nucleic acids and glycogen are soluble in aqueous solutions and precipitate (aggregate) when the dielectric constant is lowered by the added alcohol. Glycogen is also advantageously used as a carrier because it is charge-neutral and causes no inhibition of common enzymatic reactions performed with nucleic acids (e.g.: restriction digestion, cDNA synthesis, transcription, ligation, amplification, sequencing, tailing, etc.). For some applications, glycogen is preferred over tRNA, which can interfere with some enzymatic reactions such end-labeling with kinase.

Despite the wide-ranging use of nucleic acid precipitation in almost all common molecular biology methods, the technique is often prone to unpredictable failure. Even when a carrier molecule is to increase the total amount of precipitated nucleic acid, nucleic acid pellets are easily lost during the removal of supernatant phases, particularly when working with small amounts (<10 μg) of nucleic acids, or when using carriers, which are not readily visible to the unaided eye. In addition, protocols often require that nucleic acid pellets be washed with alcohol solutions and dried under vacuum prior to re-solubilization in aqueous buffers. These steps often result in the dislodging of pelleted nucleic acids which are easily lost during subsequent handling.

It would be desirable to be able to monitor the presence and location of nucleic acid during a precipitation method to prevent inadvertent loss of pelleted material.

BRIEF SUMMARY OF THE INVENTION

The present invention is summarized in that the monitoring problems recognized in the art of nucleic acid precipitation are overcome by modifying a carrier molecule to make it more visible. A modified carrier molecule having increased visibility retains the solubility and precipitation properties of the unmodified molecule, but in addition, can be readily visualized. When used as a carrier for a nucleic acid in a precipitation method, the modified carrier acts as an indicator for the presence and location of the nucleic acid.

In keeping with the invention, the carrier modified in accordance with the invention shares a generally polymeric structure with nucleic acid molecules and includes a structural site that can be modified with a suitable indicator molecule, preferably by covalent modification. The site can be one or more atoms in size. The suitable indicator molecule is readily visualized and includes a reactive group that can be coupled to the polymeric carrier. The indicator molecule is attached to the polymeric carrier using any of a variety of well understood chemical coupling methods.

The present invention is also summarized in that the modified carrier is advantageously used in a method for precipitating nucleic acid molecules. The modified carrier is added to a sample containing a nucleic acid and precipitation is then carried out in a manner known to the art. In contrast to existing methods, however, the modified carrier of the present invention co-precipitates with the nucleic acid thereby permitting the user to directly observe the location of nucleic acid in the treated sample.

It is an object of the present invention to provide a carrier molecule having the solubility and precipitation properties of nucleic acid which at the same time permits the user to visualize the progress of the precipitation.

It is an advantage of the present invention that the use of the modified carrier in a precipitation method does not adversely affect subsequent reactions performed with precipitated nucleic acids.

It is a feature of the present invention that the modified carrier can have a charge opposite to that of the nucleic acid, thereby permitting the precipitated nucleic acid to be separated from the carrier molecule by routine electrophoresis.

Other objects, advantages and features of the present invention will become apparent upon consideration of the following detailed description when read in conjunction with the accompanying drawing.

BRIEF DESCRIPTION OF THE SEVERAL VIEWS OF THE DRAWING

FIG. 1 shows a method for forming a tetramethylrhodamine-glycogen conjugate.

DETAILED DESCRIPTION OF THE INVENTION

Figure 1:
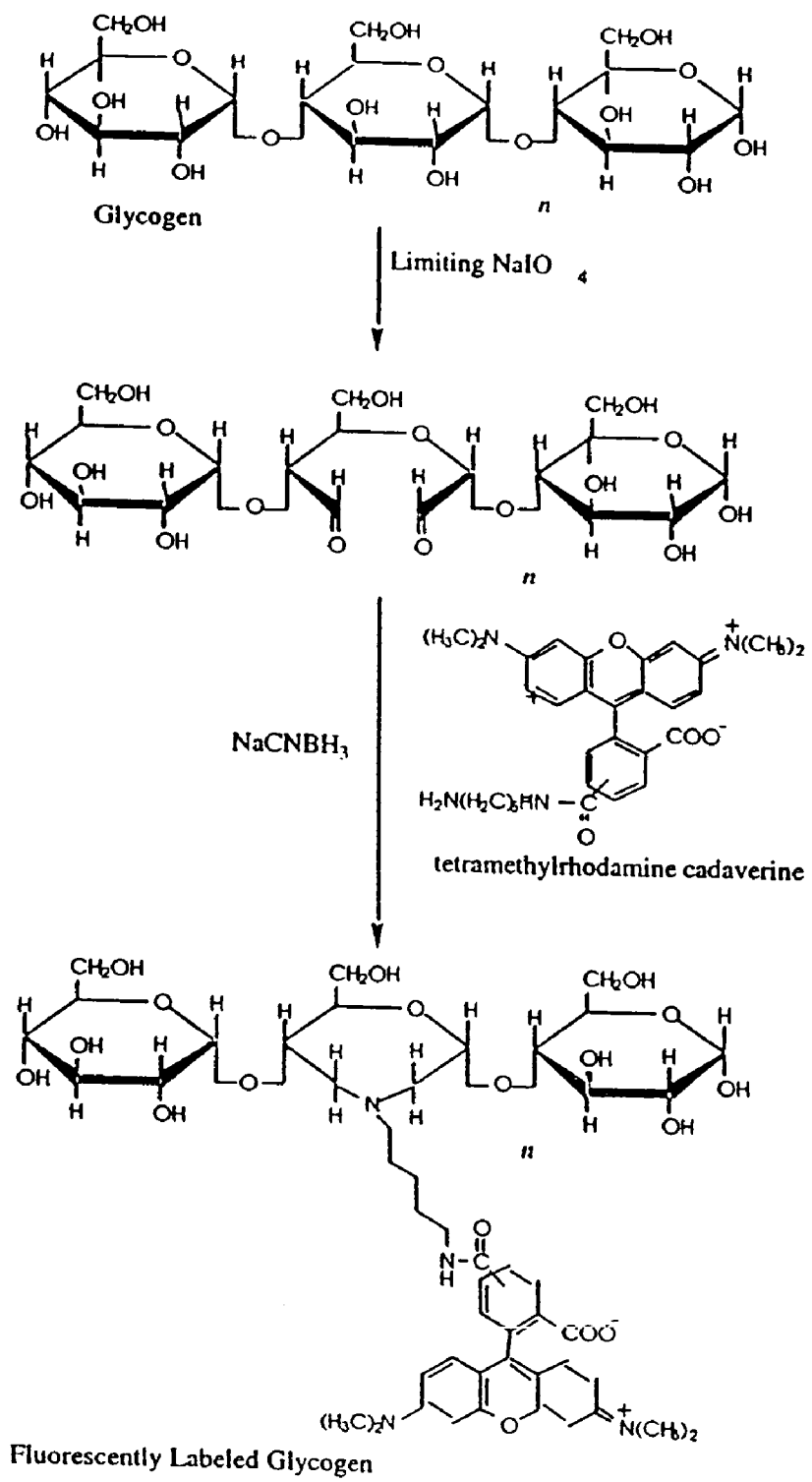
FIG. 1 shows a method for generating one embodiment of the modified carrier of the present invention. Namely.

In one aspect, the present invention is a method for precipitating nucleic acids in the presence of a carrier that is readily visualized. In the first method step, a carrier molecule coupled to an indicator molecule is added to a nucleic acid-containing sample in an aqueous solvent to be precipitated. Next, a suitable amount of salt (such as sodium chloride, sodium acetate, ammonium acetate or lithium chloride) and a suitable volume of an alcohol are added. The suitable amount of salt needed is understood in the art. It may not be necessary to add any salt if nucleic acid is present in the reaction at high amount (e.g., around 1 mg/ml or higher). Generally, the alcohol is ethanol or isopropanol. When the alcohol is ethanol, two volumes of ethanol are added to the sample volume. When the alcohol is isopropanol, 0.6 volumes of isopropanol are typically added. This aspect of the precipitation method is well understood in the art and some measure of variability in the exact ratios of aqueous sample and alcohol are acceptable to one of ordinary skill.

After the alcohol has been added, the sample is typically incubated for a suitable length of time at a suitable temperature (e.g., between room temperature and −70° C.) and then spun in a centrifuge tube to deposit the nucleic acid material along one surface of the tube. The liquid supernatant is removed, the pelleted nucleic acid is dried and resuspended for subsequent use in any of a variety of molecular biological reactions.

Wallace, supra, incorporated herein by reference, details the suitable conditions for nucleic acid precipitation. No particular adjustments to the standard precipitation method or reagents are necessary because the presence of the modified carrier does not affect the precipitation conditions.

In contrast to prior nucleic acid precipitation methods, the location of the nucleic acid in the sample will be readily apparent, because the modified carrier will distribute itself in the supernatant or precipitate with the nucleic acid.

A suitable carrier molecule is a polymeric molecule which, in its unmodified form, includes a site to which a suitable indicator molecule can be attached. In particular, vicinal hydroxides, reactive —OH group attached to adjacent carbons on a molecule, provide a site for reductive substitution of a substituent onto the molecule. Vicinal hydroxide groups, prominent in polysaccharide molecules, are desirable sites because they are readily oxidized and then coupled to a suitable indicator molecule. Other carrier molecules can include polymers having available reactive groups, such as primary amines. An example of such a polymer is linear polyacrylamide. Preferred carriers generally resemble nucleic acids in length, linear structure, solubility and precipitation properties. Crosslinking is acceptable, if it does not negatively interfere with coupling or precipitation. A sugar backbone or modified sugar backbone is desirable because of its similarity to the nucleic acid backbone. A preferred carrier is a polysaccharide. A most preferred carrier is glycogen. Glycogen is a general term encompassing polysaccharide molecules having various branching structures. A standard method for obtaining glycogen is described in Bell, D. J. and F. G. Young, *Biochem J.* 28:882 (1934). Type III glycogen from rabbit liver has been used successfully by the present inventors. Type III glycogen is available commercially from Sigma Chemical Co.

A suitable indicator molecule is any molecule, that can be coupled to a suitable carrier and can be either directly visualized or visualized by excitation with incident light of a suitable wavelength. Preferred indicators are dyes or fluorophores.

While the choice of an indicator molecule is largely dependent upon its ability to be visualized under desired conditions and upon its reactivity with carrier molecules, a preferred indicator for coupling is a primary amine-bearing dye or fluorophore. Primary amines are readily coupled, using well understood chemical coupling methods, to vicinal hydroxide groups on polysaccharide carriers. Many such primary amine-bearing compounds are commercially available. In particular, Molecular Probes, Inc., Eugene, Oreg., is a commercial source for a large number of suitable indicator molecule derivatives that can be coupled as described herein. Molecular Probes 1992–1994 catalog, incorporated herein by reference. Suitable indicator molecule precursors include, but are not limited to, the following:

5-(aminoacetamido)fluorescein(fluoresceinyl glycine amide)
4'-((aminoacetamido)methyl)fluorescein
5-aminoeosin
N-(2-aminoethyl)-4-amino-3,6-disulfo-1,8-naphthalimide, dipotassium salt
5-((2-aminoethyl)amino)naphthalene-1-sulfonic acid, sodium salt
5-((2-aminoethyl)thioureidyl)fluorescein
4'-(aminometyl)fluorescein, hydrochloride
5-(aminomethyl)fluorescein, hydrochloride
7-amino-4-methylcoumarin
1-aminomethylpyrene, hydrochloride
8-aminonaphthalene-1,3,6-trisulfonic acid, disodium salt (ANTS)
5-(and-6)-((N-(5-aminopentyl)amino)carbonyl)-tetramethylrhodamine(tetramethylrhodamine cadaverine)
5-((5-aminopentyl)thioureidyl)eosin, hydrochloride (eosin cadaverine)
5-((5-aminopentyl)thioureidyl)fluorescein (fluorescein cadaverine)
6-aminoquinoline 5-(((2-(carbohydrazino)methyl)-thio)acetyl)aminofluorescein
Cascade Blue® cadaverine, trisodium salt
Cascade Blue® ethylenediamine, trisodium salt
Cascade Blue® hydrazide, tripotassium salt
Cascade Blue® hydrazide, trisodium salt Certain fluorophores are known to photobleach and lose their indicator qualities after extended exposure to UV light. Accordingly, it is desirable to use fluorophores without additional UV illumination. Although the preferred indicator molecules are observable without the aid of incident UV light of appropriate wavelength, the inventors have observed that smaller amounts of carrier material are detectable when the samples are examined under UV light because the background fluorescence tends to be reduced.

If the indicator molecule is to be illuminated with ultraviolet (UV) light, longer wavelength UV light (greater than 300 nm) is more suitable, because these longer wavelengths are less prone to inducing cleavage in the nucleic acid strands which would also be illuminated. Moreover, the inclusion of an excitable indicator molecule in a nucleic acid reaction may actually have a protective effect on nucleic acid because the indicator molecule can adsorb UV light and emit that energy at a much higher wavelength. Therefore, incident UV light that might otherwise attack and damage nucleic acid molecules is instead captured and redirected by the indicator molecule. To avoid photobleaching, it is preferred that only brief UV exposures be used.

A preferred, coupled indicator molecule is tetramethylrhodamine which has a molar extinction co-efficient at 542 nm of 95,000 and excitation and emission maxima of 542 and 571 nm, respectively. The primary amine-bearing derivative, tetramethylrhodamine cadaverine [5-(and -6)-((N-(5-aminopentyl)amino)carbonyl)tetramethylrhodamine], contains a net positive charge at neutral pH. These three characteristics of this fluorophore provide three useful properties to the tetramethylrhodamine-glycogen conjugate as a carrier. First, to the naked eye, the visibility of any compound in solution, or in precipitated form, is proportional to the amount of light of a visible wavelength absorbed by the compound. Since tetramethylrhodamine is highly absorbant at 542 nm, the glycogen conjugate of this compound has a vivid pink appearance in both its soluble and precipitated states. This allows the addition of the reagent to be confirmed visually, in contrast to the addition of unconjugated, colorless glycogen. In addition, the precipitated form is easily visualized in normal daylight when as little as 2.5 microgram of the conjugate is precipitated.

Second, the excitation/emission spectrum for tetramethylrhodamine is well suited to fluorescent detection of precipitated conjugate by excitation with long or short wavelength UV light. Excitation of the compound with long or short wavelength UV light results in a bright orange fluorescent emission with a maximum of 571 nm. This characteristic allows nucleic acids precipitated in the presence of the glycogen-tetramethylrhodamine conjugate to be detected with increased sensitivity and to be documented by the use of a UV light source and filtered camera equipment, which is commonly available in molecular biology laboratories.

Finally, the positive charge on the glycogen conjugate causes the molecule to be drawn toward the negative electrode (cathode) during gel electrophoresis, such that it does not interfere with detection of nucleic acids which migrate toward the positive electrode (anode). Since nucleic acids and modified carrier migrate in opposite directions, ethidium bromide-stained nucleic acid bands can be easily distinguished from the fluorescent signal arising from the carrier molecule. The net positive charge on the molecule does not interfere with its function as a carrier for nucleic acid precipitation, nor does it inhibit enzymatic reactions commonly used in molecular biology.

In a more particular embodiment, it may be preferred that the indicator molecule also be responsive to changes in pH of a solution that contains the modified carrier and the nucleic acid. This may be particularly desirable when, for example, alkaline denaturation of the nucleic acid is to be accomplished before precipitation, as can be the case in preparing nucleic acid templates for certain sequencing methods. For example, in the presence of the pH-responsive indicator coupled to the carrier, a double-stranded DNA template can be denatured with 0.1M NaOH and then precipitated for use in a sequencing reaction.

It is preferred that the indicator molecule evidence a detectable change (e.g., a change from one color to another) above about pH 8.5. It is advantageous to provide a pH-responsive indicator molecule because it both permits one to track both the precipitation of DNA and provides a confirmation of denaturation prior to sequencing. It is most preferred that the indicator be detectable under both alkaline and acidic conditions, although it can be sufficient for the color to either appear or disappear when the pH transition is accomplished. In addition, pH-responsive coupled indicators may be visible without illumination that can harm nucleic acid. It is preferred, but not essential, that the color change be visible to the naked eye. Spectrophotometric detection can also be suitable, if reactions are to be carried out in an automatic processing system.

It is noted that Molecular Probes, Inc., Eugene, Oreg., makes commercially available a set of pH indicator molecules which are offered for use in determining intracellular pH. Molecular Probes 1992–1994 catalog, incorporated herein by reference. The pH indicator molecules noted therein may have advantageous properties when employed as pH-responsive indicators in the present invention. At least two of the pH indicator compounds available from Molecular Probes are provided as succinimidyl esters (Catalog items #3061 and #3062) which can readily be covalently attached to glycogen modified by periodate oxidation followed by reductive amination coupling of ethylene diamene. The modified glycogen will bear a coating of reactive primary amines for subsequent reaction with the succinimidyl esters.

The method for coupling the indicator to the carrier can be any suitable conjugation method selected to accommodate the particular reactive sites on the carrier and the indicator. Because of their particular reactivity, it is preferred that the indicator molecule include a primary amine group that can readily substitute into the polymeric backbone of the carrier at the site of the vicinal hydroxides. It is also possible to indirectly couple an indicator molecule to a carrier. This could be performed, for example, by covalently coupling a biotinylated primary amine to the carrier and subsequently adding a fluorescent avidin derivative. One of ordinary skill will appreciate that direct coupling is less burdensome, but that any number of other labelling techniques can readily be envisioned to accomplish the goal of coupling a carrier molecule and an indicator molecule.

A suitable method is shown in FIG. 1. The modified carrier can be activated for substitution by first treating the polymer containing vicinal hydroxides with a limiting treatment of periodate, preferably in the form of sodium-metaperiodate (NaIO$_4$) to break the C—C bond between the carbons bearing the vicinal hydroxide groups. When this bond is broken, amine-reactive aldehydes are generated. The amine reactive aldehydes of the carrier molecule are then coupled via Schiff's base formation to primary amine functional groups present on the indicator molecule. The Schiff's bases thus formed are reduced with sodium cyanoborohydride. This reductive amination process has been used to immobilize proteins on polysaccharide supports for other purposes. See, e.g., Hermanson, G. T. et al. in Immobilized Affinity Ligand Techniques, 69–77, Academic Press (1992) and Dean, P. D. G. et al., eds., Affinity Chromatography: A practical approach, 44–48, IRL Press (1985). This same chemistry has also been used to selectively methylate the C-2 and C-3 positions of the glucose residues of glycogen. Bahl, O. P. and F. J. Smith, 31 Org. Chem. 2915–2920 (1966).

A related method can be used to join the pH-responsive indicator molecule to the carrier molecule. In a suitable method, glycogen is oxidized with 0.1M–0.2M sodium metaperiodate for 1–2 hours at room temperature, then is precipitated with an equal volume of isopropanol or two volumes of ethanol, and then is resuspended in deionized water to about 10 mg/ml. The indicator solution is prepared by scaling up the method of Lillie, R. D. and Fullmer, H. M., *Histopathic Technic and Practical Histochemistry*, 4th Ed., McGraw-Hill, NY (1976), cited in Williams and Wilkens, *Staining Procedures*, 4th Ed. (1981), both books being incorporated herein by reference. Briefly, 1 g of parosoaniline (Sigma) is dissolved in 80 ml of deionized water. Then, 2 g of $NaHSO_4$ is added, followed by 20 ml 1N HCl. The mixture is mixed and incubated for two hours with periodic mixing. Next, 500 mg of powdered charcoal can be added, shaken for 1 minute, and filtered through Whatman filter paper. Aliquots of oxidized glycogen are combined with varying amounts of the indicator solution and are allowed to react for 10 to 60 minutes. The resultant indicator-labeled glycogen is precipitated with an equal volume of isopropanol, washed with 70% ethanol and dried. Following resuspension in water, the compound is tested for detectability upon precipitation, solidity of pelleted material, and pH sensitivity. Glycogen labeled with parosoaniline prepared in this manner has been successfully used in the nucleic acid precipitation method of the present invention and have shown acceptable response to changes in solution pH. It is expected that New Fuchsin (Sigma) will also function well in this assay since it is a dye that is structurally related to parosoaniline that is used interchangeably in histological staining techniques.

Other methods for joining molecules to the carrier molecule, are available to those skilled in the art. The selection of a particular method will depend upon the reactive groups available on the indicator and carrier molecules.

It is important that the level of carrier activation and indicator coupling be selected with care to maintain the solubility characteristics of the parent carrier molecule. For example, in the exemplified embodiment of FIG. 1, the glycogen carrier is coupled to tetramethylrhodamine, a highly fluorescent pink fluorophore. The indicator molecule is provided in the form of tetramethylrhodamine cadaverine, the structure of which is also shown in FIG. 1. The first important limit on the process is the amount of sodium metaperiodate used to treat the parent carrier molecule. The applicants have determined that when the carrier is treated with an excessive amount of periodate (e.g., greater than 0.5 M for 30 min.), the resulting coupled compound exhibits poor precipitation and does not co-precipitate with the nucleic acid. The amount of periodate used has a direct effect upon the amount of indicator molecule that can be coupled to the carrier. Since the role of the periodate is to break a C—C bond in the sugar ring of the backbone, the amount of bond breakage is directly proportional to the number of sites available for conjugation. Accordingly, a simple stoichiometric calculation can be performed once one has determined the suitable level of conjugation. The applicants have determined that when more than 10% of the glucose moieties are activated by the periodate, poor precipitation results. The applicants have further determined that activation of 10% or less of the glucose moieties is suitable. Activation of, and subsequent coupling to, 10% of the glucose moieties is a preferred level of conjugation that yields a carrier molecule having the desired precipitation properties.

The duration of the oxidation reaction is also important to the periodate activation of the carrier. In preliminary experiments using glycogen, when the length of oxidation time was varied from 30 minutes to overnight, it was observed that at long treatment times, the conjugate did not fully precipitate and soft pellets, which adhered poorly to tube walls, were formed. At a 30 minute reaction time, the labelled conjugate brought about quantitative precipitation and solid pellets. These preliminary experiments sought a stoichiometric activation ratio of 1 periodate per 10 glucose units in the glycogen carrier. However, it is thought that the activation reaction is not complete after 30 minutes, but is complete after an overnight incubation. Thus, reaction times greater than 30 minutes, but less than overnight might also be suitable.

These values have been determined using glycogen as the carrier and conjugated tetramethylrhodamine as the indicator. It is likely that when other molecules are employed, variation in the precipitation properties may be observed. Therefore, the conjugation strategy herein described should be regarded as guidelines, but simple experimentation to determine the suitable extent of conjugation for a particular carrier with a particular indicator is recommended. It is hypothesized that for polysaccharide carrier parent molecules, the chain length and the extent of cross-linking could also affect the precipitation properties of the resulting modified carrier.

It is also possible that other methods can be used to couple a fluorophore to glycogen. It would be possible to convert a limited number of the available hydroxyls on the glycogen to a non-endogenous functional group (such as a primary amine, sulfhydryl, or carboxylic acid and then to react the converted glycogen with an appropriate activated fluorophore that specifically reacts with the added functional group. Numerous fluorophore-labeled molecules capable of such specific reactivity are commercially available, for example, Molecular Probes, Inc. These reagents include labeled isothiocyanates, maleimides, haloacetyls, bromomethyls, acryloyls, succinimidyl esters, and sulfonyl chlorides. Methods for converting hydroxyl groups to sulfhydryl groups and for converting sulfhydryl groups to primary amines are described in Wong, S. S. Chemistry of Protein Conjugation and Cross-Linking, CRC Press, Boca Raton, Fla. 21–25 (1993), which is incorporated herein by reference.

It may also be possible to activate glycogen using cyanogen bromide as described in Wong, supra, by forming a cyclic, reactive imidocarbonate from the vicinal hydroxyls. This product rearranges to form N-substituted carbamate as the end product.

It is understood that, by their nature, polysaccharides, including glycogen, can vary in structure depending upon their method of preparation. The applicants have determined that when the carrier parent molecules, or the conjugated molecules, are excessively or vigorously treated during preparation, their precipitation properties can vary and can become unacceptable. Therefore, it is recommended that if glycogen is used as a carrier that it be Type III glycogen, which is commercially available from Sigma Chemical Co. Type III glycogen is herein shown to be suitable. Other glycogen preparations may also be suitable. Likewise, when resuspending a precipitated conjugated molecule, it is important that it be treated gently to retain the solubility and precipitation characteristics for subsequent treatment steps. Thus no vortex or Dounce homogenizing steps should be used. The inventor has found that when preparing indicator-conjugated carrier, it is preferable that the carrier not be conjugated, to avoid shearing forces. However, such small amounts of the conjugated carrier are used in nucleic acid precipitation methods that short vortexinq steps are tolerated. If desired, a precipitate pellet can be gently broken from the wall of the sample tube and then rocked overnight at 4° C., to resuspend the pellet. This procedure is recommended particularly if the nucleic acid sample will be subjected to several precipitation steps.

The use of a modified carrier of the type herein described in a nucleic acid precipitation method provides the ability to monitor the location of the precipitated nucleic acids because of the highly visible carrier. This improvement to existing precipitation methods can greatly reduce or eliminate potential losses of precipitated nucleic acids, thereby making the invention extremely useful and valuable as a general purpose molecular biology tool.

EXAMPLE 1

Preparation of Fluorescently Labeled Glycogen 1 gram of glycogen was carefully weighed and was added to 40 ml of sterile water in a sterile 50 ml conical tube. The tube was placed on a shaking platform and shaken gently until the glycogen was fully resuspended. Sodium meta periodate (114 mg) was added to the glycogen suspension. To achieve complete transfer, the weight boat on which the periodate was measured was washed several times with the glycogen solution which was then returned to the conical tube. The periodate-glycogen mixture was incubated at room temperature for 30 minutes.

The mixture was split evenly into two 50 ml tubes. Absolute ethanol (35 ml) was added to each tube. The tubes were inverted several times to mix. A white precipitate formed upon mixing.

The tubes were spun at 3000× g for 5 minutes to pellet the white precipitate. Each pellet was resuspended in 20 ml of sterile Milli-Q water. Resuspension was performed without vortexing or triturating the pelleted material. The tube was placed on a shaking table and incubated overnight at room temperature.

The contents of the two tubes were pooled and 5 ml of 1×PBS, pH 7.4, was added. A tetramethylrhodamine stock solution was prepared by solubilizing 10 mg tetramethylrhodamine cadaverine in 1 ml of ethanol (in an amber vial) with vortexing. 300 µl of the tetramethylrhodamine cadaverine stock solution were added to the oxidized glycogen solution and were mixed by inversion several times. Sodium cyanoborohydride (5 ml of 1 M in sterile Milli-Q water) was added to the mixture of tetramethylrhodamine and oxidized glycogen and was inverted several times to mix. The tube was placed on a shaking table and incubated overnight at room temperature.

The reaction was then split into two 50 ml conical tubes and 1/10 volume of 3 M ammonium acetate, pH 5.2, was added to each tube. Isopropanol (0.6 volumes) was then added and mixed by inversion. A cloudy, pink precipitate was evident. The tubes were spun at 3000× g for 5 minutes at room temperature.

A firm, bright pink pellet and a clear pink supernatant were observed. The supernatant was decanted and the pellet was washed several times with 70% ethanol and spun at 3000× g for 5 minutes at room temperature to repellet the conjugated material. The pellet was washed in 100% ethanol several times to remove excess water and spun as necessary to retain the pelleted material. The final supernatant was decanted and the tube was inverted on a clean paper towel and allowed to drain for 5–10 minutes. The pellet remained firmly adhered to the tube.

The tube was capped loosely and placed in a speed-vac with rotor removed. A vacuum was slowly drawn and was maintained for one hour. The pellet detached from the wall of the tube and caution was used while removing the tube from the speed-vac. The mass of the fluorescent glycogen conjugate was recorded. In several experiments, the mass was typically 50–70% of the initial glycogen mass. The conjugate was resuspended to a concentration of 10 mg/ml in DEPC-treated Milli-Q water. This resuspension was done without vortexing for several hours on the shaker table. The conjugate was safely stored, wrapped in foil, at −20° C.

The present invention is not to be limited to the preceding embodiments, but rather to encompass all such modifications and variations as come within the scope of the appended claims.

I claim:

1. A method for precipitating unprecipitated nucleic acid from an aqueous solution, the method comprising the step of adding to the solution a polymeric carrier molecule coupled to an indicator molecule, and an amount of a salt and an amount of an alcohol sufficient to precipitate the nucleic acid from the solution.

2. A method as claimed in claim 1 wherein the carrier molecule is covalently attached to the indicator molecule.

3. A method as claimed in claim 1 wherein the carrier molecule is covalently attached to the indicator molecule by reductively substituting the indicator molecule at a pair of vicinal hydroxides on the carrier molecule.

4. A method as claimed in claim 1 wherein the carrier molecule is a polysaccharide.

5. A method as claimed in claim 1 wherein the carrier molecule is a glycogen.

6. A method as claimed in claim 1 wherein the carrier molecule is Type III glycogen.

7. A method as claimed in claim 1 wherein the indicator molecule is selected from a group consisting of a dye and a fluorophore.

8. A method as claimed in claim 1 wherein the indicator molecule and the carrier molecule are coupled via an amine linkage.

9. A method as claimed in claim 1 wherein the indicator molecule is selected from a group consisting of 5-(aminoacetamido)fluorescein(fluoresceinyl glycine amide), 4'-((aminoacetamido)methyl)fluorescein, 5-aminoeosin, N-(2-aminoethyl)-4-amino-3,6-disulfo-1,8naphthalimide dipotassium salt, 5-((2-aminoethyl)amino)naphthalene-1-sulfonic acid sodium salt, 5-((2-aminoethyl)thioureidyl) fluorescein, 4'-(aminometyl) fluorescein hydrochloride, 5(aminomethyl)fluorescein hydrochloride, 7-amino-4-meth ylcoumarin, 1-ainomethylpyrene hydrochloride, 8-aminonaphthalene-1,3,6-trisulfonic acid disodium salt (ANTS), 5-(and-6)-((N-(5-aminopentyl)amino)carbonyl)-tetramethylrhodamine(tetramethylrhodamine cadaverine), 5((5-aminopentyl)thioureidyl)eosin hydrochloride(eosin cadaverine), 5-((5-aminopentyl)thioureidyl)fluorescein(fluorescein cadaverine), 6-aminoquinoline, 5((2-(carbohydrazino)methyl)-thio)acetyl)aminofluorescein, Cascade Blue cadaverine trisodium salt, Cascade Blue ethylenediamine trisodium salt, Cascade Blue hydrazide tripotassium salt, and Cascade Blue hydrazide trisodium salt.

10. A method as claimed in claim 1 wherein the indicator molecule is 5-(and-6)-((N-(5-aminopentyl)amino)carbonyl)-tetramethyirhodamine(tetramethylrhodamine cadaverine).

11. A method as claimed in claim 1 wherein the indicator molecule is a pH-responsive indicator molecule.

12. A method as claimed in claim 1 wherein the pH-responsive indicator molecule is selected from a group consisting of parosoaniline, New Fuchsin, and a succinimidyl ester.

* * * * *

UNITED STATES PATENT AND TRADEMARK OFFICE
CERTIFICATE OF CORRECTION

PATENT NO.          : 7,144,713 B1                                  Page 1 of 1
APPLICATION NO.  : 08/724631
DATED                  : December 5, 2006
INVENTOR(S)         : Mark R. McCormick It is certified that error appears in the above-identified patent and that said Letters Patent is hereby corrected as shown below:

Col. 11, line 6, Claim 9:

Delete "5((2-carbohydrazino) . . ." and replace it with --5-(((2-(carbohydrazino) . . .--.

Col. 12, line 3, Claim 10:

Delete "tetramethyirhodamine" and replace it with --tetramethylrhodamine--.

Signed and Sealed this

First Day of April, 2008

JON W. DUDAS
*Director of the United States Patent and Trademark Office*